(12) United States Patent
Fujinaga et al.

(10) Patent No.: US 8,968,779 B2
(45) Date of Patent: Mar. 3, 2015

(54) CONTROLLED RELEASE COAT-CORE TABLET

(75) Inventors: Kentaro Fujinaga, Hino (JP); Susumu Maruo, Hino (JP); Hideaki Nakamura, Hino (JP); Kenji Sunagawa, Iwakuni (JP); Tsutomu Mochizuki, Hino (JP); Michiharu Kageyama, Hino (JP)

(73) Assignee: Teijin Pharma Limited, Tokyo (JP)

( * ) Notice: Subject to any disclaimer, the term of this patent is extended or adjusted under 35 U.S.C. 154(b) by 0 days.

(21) Appl. No.: 13/704,345

(22) PCT Filed: Jun. 15, 2011

(86) PCT No.: PCT/JP2011/063713
§ 371 (c)(1),
(2), (4) Date: Dec. 14, 2012

(87) PCT Pub. No.: WO2011/158870
PCT Pub. Date: Dec. 22, 2011

(65) Prior Publication Data
US 2013/0089609 A1    Apr. 11, 2013

(30) Foreign Application Priority Data

Jun. 16, 2010 (JP) ................................. 2010-137322
Jun. 16, 2010 (JP) ................................. 2010-137323

(51) Int. Cl.
| A61K 9/24 | (2006.01) |
| A61K 9/28 | (2006.01) |
| A61K 31/426 | (2006.01) |
| A61K 9/20 | (2006.01) |

(52) U.S. Cl.
CPC ............... *A61K 9/2866* (2013.01); *A61K 9/209* (2013.01); *A61K 31/426* (2013.01); *A61K 9/2018* (2013.01); *A61K 9/2054* (2013.01)
USPC ........................................................ 424/472

(58) Field of Classification Search
None
See application file for complete search history.

(56) References Cited

U.S. PATENT DOCUMENTS

| 5,861,173 | A | 1/1999 | Nishioka et al. |
| 6,410,054 | B1 * | 6/2002 | Thosar et al. ................. 424/489 |
| 7,361,676 | B2 * | 4/2008 | Iwai et al. ...................... 514/365 |
| 2002/0058066 | A1 | 5/2002 | Tomohira et al. |
| 2005/0043375 | A1 * | 2/2005 | Iwai et al. ...................... 514/365 |
| 2008/0026052 | A1 * | 1/2008 | Schoenhard ................... 424/456 |
| 2009/0110726 | A1 * | 4/2009 | Narasaki et al. .............. 424/467 |
| 2009/0117182 | A1 * | 5/2009 | Akutagawa et al. .......... 424/464 |
| 2009/0175959 | A1 | 7/2009 | Brando et al. |
| 2010/0172988 | A1 | 7/2010 | Takeda et al. |
| 2010/0221335 | A1 | 9/2010 | Kanamaru et al. |
| 2010/0239667 | A1 * | 9/2010 | Hemmingsen et al. ....... 424/466 |
| 2010/0316711 | A1 | 12/2010 | Yamanouchi et al. |
| 2011/0046192 | A1 * | 2/2011 | Shirakura et al. ............. 514/370 |
| 2011/0311620 | A1 * | 12/2011 | Taneja et al. .................. 424/462 |

FOREIGN PATENT DOCUMENTS

| CN | 101658505 A | 3/2010 |
| CN | 101671315 A | 3/2010 |
| EP | 1915989 | 4/2008 |
| JP | 9-143073 A | 6/1997 |
| JP | 2002-97132 A | 4/2002 |
| JP | 2002535310 | 8/2002 |
| JP | 2003-95948 A | 4/2003 |
| JP | 2003-267889 A | 9/2003 |
| JP | 2004-2348 A | 1/2004 |
| JP | 2009-120600 A | 6/2009 |
| WO | 0018373 | 4/2000 |
| WO | 2007074909 | 7/2007 |
| WO | 2007080776 | 7/2007 |
| WO | 2009/028598 A1 | 3/2009 |

OTHER PUBLICATIONS

Communication for EP 11795774.6 dated Nov. 4, 2013, with Supplementary European Search Report.

* cited by examiner

*Primary Examiner* — Robert A Wax
*Assistant Examiner* — Olga V Tcherkasskaya
(74) *Attorney, Agent, or Firm* — Sughrue Mion, PLLC

(57) ABSTRACT

Disclosed is a controlled release nucleated tablet which is composed of an inner nucleus and an outer layer that covers the inner nucleus and is capable of maintaining the level of 2-(3-cyano-4-isobutyloxyphenyl)-4-methyl-5-thiazolecarboxylic acid in the blood to a certain value or higher for a long period of time. The controlled release nucleated tablet is characterized in that the inner nucleus contains 2-(3-cyano-4-isobutyloxyphenyl)-4-methyl-5-thiazolecarboxylic acid and the outer layer contains 2-(3-cyano-4-isobutyloxyphenyl)-4-methyl-5-thiazolecarboxylic acid and a gel-forming water-soluble polymer that is in an amount of 16 (w/w) % or more relative to the weight of the outer layer.

16 Claims, 6 Drawing Sheets

CONTROLLED RELEASE COAT-CORE TABLET

CROSS REFERENCE TO RELATED APPLICATIONS

This application is a National Stage of International Application No. PCT/JP2011/063713, filed on Jun. 16, 2011, which claims priority from Japanese Patent Application Nos. 2010-137322 and 2010-137323, both filed on Jun. 16, 2010, the contents of all of which are incorporated herein by reference in their entirety.

TECHNICAL FIELD

The present invention relates to a controlled release coat-core tablet that can maintain the concentration of 2-(3-cyano-4-isobutyloxyphenyl)-4-methyl-5-thiazole carboxylic acid in the blood at a certain level or higher over a long period of time.

BACKGROUND ART 2-(3-Cyano-4-isobutyloxyphenyl)-4-methyl-5-thiazole carboxylic acid (hereinbelow sometimes referred to as Compound I) exhibits a potent xanthine oxidase inhibitory activity and an effect of decreasing uric acid in vivo and it has been marketed as a drug for the treatment of gout and an increased uric acid level. This Compound I is generally administered orally in the form of a tablet prepared by tabletting together with additives such as excipients; however, conventional tablets are immediate release tablets, with which the concentration of the drug rises in a short time, while maintenance of the concentration at a certain level or higher over a long period of time has been difficult. A sustained release preparation from which a drug is released gradually can be considered as one of the methods used when the blood concentration must be maintained at a certain level or higher over a long period of time.

A single-component matrix type sustained release preparation and a controlled release preparation using a coating film, a routine method, have been known as sustained release preparations and these preparations are expected to be able to maintain the blood concentration over a long period of time by releasing a drug gradually at a constant rate.

Further, preparations having a bimodal drug release profile to maintain and regulate the drug concentration in blood over a long period of time are also known, from which a drug is released rapidly when release starts and then gradually after a certain time, or on the contrary, a drug is released gradually when release starts and then rapidly after a certain time. A coat-core sustained release tablet is one of the dosage forms that enable such multiple-phase drug release.

Patent Literature 1 (Japanese Patent No. 2955524) describes a coat-core sustained release tablet of nifedipine, wherein an inner core (core portion) is an immediate release tablet and an outer layer portion is a sustained release matrix layer from which a drug is dissolved slowly so that a decrease in release rate due to a decrease in a volume is avoided.

Patent Literature 2 (Japanese Patent No. 3220373) describes a coat-core sustained release tablet of nifedipine with improved resistance to environment in the digestive tract having a strong mechanical stimulation, wherein an inner core (core portion) is a sustained release matrix tablet and an outer layer portion is a sustained release matrix containing a disintegration suppressing molecule from which a drug is dissolved slowly.

Patent Literature 3 (Japanese Patent No. 3751287) describes a small-sized coat-core sustained release tablet of nifedipine comprising a sustained release matrix from which a drug is dissolved slowly, wherein an inner core and an outer layer portion contain a disintegration suppressing molecule.

Patent Literature 4 (Japanese Patent No. 4637338) describes a solid coat-core preparation of cilostazol, wherein an inner core (core portion) is a sustained release matrix tablet from which a drug is dissolved rapidly and an outer layer portion is a sustained release matrix containing a water-insoluble substance from which a drug is dissolved slowly.

Patent Literature 5 (Japanese Patent Application Laid-open No. 2011-63611) describes a solid coat-core preparation of cilostazol, wherein an inner core (core portion) is a tablet containing a surfactant and an outer layer portion is a sustained release matrix from which a drug is dissolved slowly. This coat-core tablet is a preparation characterized by incorporating a surfactant in the inner core to improve the solubility of cilostazol and improve absorption of the drug from the regions ranging from the small intestine to the colon, the lower part of the digestive tract.

CITATION LIST

Patent Literature

Patent Literature 1] Japanese Patent No. 2955524
[Patent Literature 2] Japanese Patent No. 3220373
[Patent Literature 3] Japanese Patent No. 3751287
[Patent Literature 4] Japanese Patent No. 4637338
[Patent Literature 5] Japanese Patent Application Laid-open No. 2011-63611

SUMMARY OF INVENTION

Technical Problem

Coat-core sustained release tablets have conventionally been designed considering the influence of mechanical destructive force generated by peristaltic movements of the digestive tract and eating, and considering a decrease in dissolution rate due to a decrease in a surface area of a preparation in the late phase of dissolution. At the same time, pH environment in the digestive tract is known to vary largely from the stomach to the lower part of the small intestine, and such changes in the environment may affect the dissolution of an active ingredient.

An object of the present invention is to provide a sustained release preparation that can release Compound I stably in the region ranging from the stomach to the lower part of the small intestine where the pH environment varies widely.

Another object of the present invention is to provide a sustained release preparation, with which Compound I is released stably in the region ranging from the stomach to the lower part of the small intestine where the pH environment varies widely and then remaining Compound I is released rapidly in the colon containing a small amount of water to enable maintenance of the drug concentration in the blood over a long period of time.

A further object of the present invention is to provide a sustained release preparation that enables maintenance of the drug concentration in the blood over a long period of time by releasing Compound I stably in the region ranging from the stomach to the lower part of the small intestine where the pH environment varies widely and then improving the absorption rate of remaining Compound I in the colon.

Solution to Problem

The present inventors have keenly conducted investigation in view of the above technical problems and, as a result, found that Compound I can be released stably without burst in the region ranging from the stomach to the lower part of the small intestine where the pH environment varies widely by using a specific composition for a layer containing Compound I.

In other words, the present invention is a controlled release coat-core tablet comprising an inner core and an outer layer portion covering the inner core, wherein the inner core contains Compound I and the outer layer portion contains Compound I and a water-soluble polymer in an amount of 16% (w/w) or more with respect to the weight of the outer layer portion.

Advantageous Effects of Invention

The preparation according to the present invention can regulate and maintain blood concentrations of Compound I over a long period of time by releasing Compound I at a constant rate in the region ranging from the stomach to the lower part of the small intestine where the pH environment varies widely.

The preparation according to the present invention also has excellent compression moldability.

DESCRIPTION OF EMBODIMENTS

Figure 1:
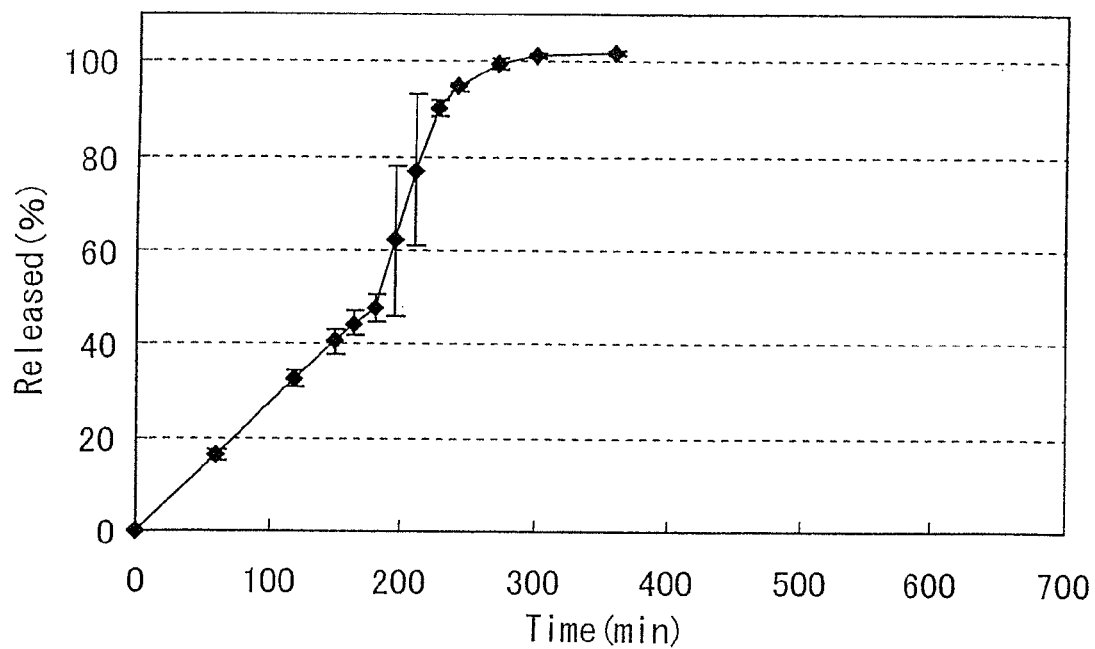
FIG. 1 shows the results of the dissolution test of Example 1, Test Example 1 (average of N=3).

The outer layer portion of the coat-core tablet of the present invention is a sustained release matrix layer and contains Compound I and a gel-forming water-soluble polymer. The outer layer portion may contain the gel-forming water-soluble polymer in an amount of 16% (w/w) or more, preferably in an amount of 18% (w/w) or more, more preferably in the range of 20 to 60% (w/w), further preferably 20 to 55% (w/w), and further more preferably 35 to 45% (w/w) with respect to the weight of the outer layer portion. When the content of the water-soluble polymer is 15% (w/w) or lower, the outer layer portion is rapidly eroded and disintegrated at a pH value higher than neutral and the dissolution rate of Compound I is elevated, resulting in occasional occurrence of burst, which is not preferable. When the content is within the above-mentioned range, erosion or disintegration of the outer layer portion is insusceptible to the influence of mechanical disintegration force such as peristaltic movements of the digestive tract and eating and changes in pH in the digestive tract so that Compound I can be released at a constant rate. A water-insoluble polymer having an effect of suppressing disintegration may be added at that time, but it is preferable not to add such a polymer.

The gel-forming water-soluble polymer is a water-soluble polymer that swells and becomes gel upon contact with water, and includes, for example, hydroxypropylcellulose, hydroxypropylmethylcellulose, carmellose, carmellose sodium, methylcellulose, hydroxyethylcellulose, hydroxyethylmethylcellulose, pregelatinized starch, sodium alginate, gelatin, agar, tragacanth, xanthan gum, guar gum, gum arabic, carrageenan, carboxy vinyl polymer, polyethylene oxide, vinyl acetate povidone polymer matrix, polyvinyl alcohol, polyvinylpyrrolidone, Pullulan, sodium polyacrylate, and polyoxyethylene(160)polyoxypropylene(30)glycol, which may be used singly or in combination of two or more. Among the gel-forming water-soluble polymers described above, hydroxypropylcellulose, hydroxypropylmethylcellulose methylcellulose, sodium alginate, carboxyvinyl polymer, and carmellose sodium are preferable, and hydroxypropylmethylcellulose, hydroxypropylcellulose, sodium alginate, carboxyvinyl polymer, and carmellose sodium are more preferable, and hydroxypropylmethylcellulose is particularly preferable.

Sodium alginate having a grade of about 900 to about 1,110 mPa·s in terms of a viscosity of a 1% (w/v) aqueous solution at 20° C. at pH 6.4-7.0 measured by BL type cylinder rheometer may be preferably used. Carboxyvinyl polymer having a grade of about 4,000 to about 11,000 mPa·s or that of about 29,400 to about 39,400 in terms of a viscosity of a 0.5% (w/v) aqueous solution at pH 7.5 specified by the viscosity testing method for carboxyvinyl polymer of Japanese Pharmaceutical Excipients can be use and that of about 29,400 to about 39,400 in terms of a viscosity of a 0.5% (w/v) aqueous solution at pH 7.5 is preferable. Carmellose sodium having a grade of about 320 mPa·s in terms of a viscosity of a 1% (w/w) aqueous solution measured by B type rheometer may be preferably used. Hydroxypropylcellulose having a grade of about 150 to about 400 mPa·s or that of about 1,000 to about 4,000 mPa·s in terms of a viscosity of a 2% (w/w) aqueous solution may be preferably used singly or in combination of the two at any weight ratio.

There are various viscosity grades of hydroxypropylmethylcellulose determined by the hypromellose viscosity test of the Japanese Pharmacopoeia. As regards the viscosity grade of hydropropylmethylcellulose in the outer layer portion, a grade of about 40 to 60 mPa·s, or a grade of about 80 to about 120 mPa·s, or a grade of about 320 to about 480 mPa s, or a grade of about 3,000 to about 5,600 mPa·s, or a grade of about 7,500 to about 14,000 mPa·s, or a grade of about 11,250 to about 21,000 mPa·s, or a grade of about 75,000 to about 140,000 mPa·s in terms of a viscosity of a 2% (w/w) aqueous solution at 20° C. may be used. Hydroxypropylmethylcellulose having any of these viscosity grades may be used singly or multiple types of hydroxypropylmethylcellulose having these viscosity grades may be mixed at any weight ratio and incorporated in the outer layer portion. Desirably, however, it is preferable to use hydroxypropylmethylcellulose having a grade of about 40 to 60 mPa·s, or a grade of about 80 to about 120 mPa·s, or a grade of about 320 to about 480 mPa·s, or a grade of about 3,000 to about 5,600 mPa·s, or a grade of about 7,500 to about 14,000 mPa·s in terms of a viscosity of a 2%

(w/w) aqueous solution at 20° C.; more preferably to use hydroxypropylmethylcellulose having a grade of about 40 to 60 mPa·s, or a grade of about 80 to about 120 mPa·s, or a grade of about 320 to about 480 mPa·s, or a grade of about 3,000 to about 5,600 mPa·s in terms of a viscosity of a 2% (w/w) aqueous solution at 20° C.; further more preferably to use hydroxypropylmethylcellulose having a grade of about 80 to about 120 mPa·s or a grade of about 3,000 to about 5,600 mPa·s in terms of a viscosity of a 2% (w/w) aqueous solution at 20° C., which can be used singly or mixed at any weight ratio and incorporated in the outer layer portion.

Desirably, the outer layer portion contains hydroxypropylmethylcellulose having a grade of about 80 to about 120 mPa·s in terms of a viscosity of a 2% (w/w) aqueous solution at 20° C. in an amount of 16% (w/w) or more, preferably in an amount of 18% (w/w) or more, more preferably in the range of 20 to 60% (w/w), further preferably 20 to 55% (w/w), and further more preferably 35 to 45% (w/w) with respect to the weight of the outer layer portion; or hydroxypropylmethylcellulose having a grade of about 80 to about 120 mPa·s in terms of a viscosity of a 2% (w/w) aqueous solution at 20° C. in an amount of 8% (w/w) or more, preferably in an amount of 9% (w/w) or more, more preferably in the range of 10 to 30% (w/w), further preferably 10 to 27.5% (w/w), and further more preferably 17.5 to 22.5% (w/w) with respect to the weight of the outer layer portion in mixture with hydroxypropylmethylcellulose having a grade of about 3,000 to about 5,600 mPa·s in terms of a viscosity of a 2% (w/w) aqueous solution at 20° C. in an amount of 8% (w/w) or more, preferably in an amount of 9% (w/w) or more, more preferably in the range of 10 to 30% (w/w), further preferably 10 to 27.5% (w/w), and further more preferably 17.5 to 22.5% (w/w) with respect to the weight of the outer layer portion.

The final composition of the gel-forming water-soluble polymer(s) used in the outer layer portion in terms of the type and viscosity grade is desirably adjusted to achieve the dissolution rates of Compound I determined by the dissolution test using modified paddle method of the dissolution test of the Japanese Pharmacopoeia with a stationary basket as follows:
5 to 30%, preferably 5 to 25%, more preferably 10 to 20% at 60 minutes later,
25 to 55%, preferably 30 to 50%, more preferably 35 to 45% at 150 minutes later,
70% or higher, preferably 80% or higher, more preferably 85% at 240 minutes later; or to achieve the dissolution rates of Compound I determined by the dissolution test using modified paddle method of the dissolution test of the Japanese Pharmacopoeia with a stationary basket as follows:
5 to 30%, preferably 5 to 25%, more preferably 10 to 20% at 120 minutes later,
25 to 55%, preferably 30 to 50%, more preferably 35 to 45% at 300 minutes later,
70% or higher, preferably 80% or higher, more preferably 85% or higher at 480 minutes later.

The dissolution test using modified paddle method of the dissolution test of the Japanese Pharmacopoeia with a stationary basket used in the present specification was conducted under the following conditions:
Test fluid: 900 mL of diluted McIlvaine buffer at pH 6.0
Temperature: 37° C.
Number of rotation: 200 rotations/minute
Stationary basket: A 40-mesh basket is fixed at the position in the middle between the surface of a test fluid and the bottom of a vessel and about 23 mm from the side wall of a vessel of the dissolution test fluid.

The water-insoluble polymer that is a molecule having an effect of suppressing disintegration includes, for example, ethylcellulose, cellulose acetate, aminoalkyl methacrylate copolymers RS, polylactic acid, and polyglycolic acid.

Further, the outer layer may contain, in addition to the gel-forming water-soluble polymer, as required, for example, sugars such as lactose, white sugar, glucose, fructose, trehalose, mannitol, sorbitol, xylitol, maltitol, and erythritol; starches, such as wheat starch, corn starch, potato starch, partly pregelatinized starch, dextrin, hydroxypropyl starch, and carboxymethyl starch; celluloses such as microcrystalline cellulose; inorganic salts such as light anhydrous silicic acid, synthetic aluminum silicate, magnesium aluminometasilicate, and calcium phosphate; fats and oils such as paraffin, waxes, and higher fatty acids; disintegrants such as carmellose, carmellose sodium, croscarmellose sodium, carmellose calcium, starches, crospovidone, low-substituted hydroxypropylcellulose, microcrystalline cellulose, and powder cellulose; binders such as hydroxypropylcellulose and polyvinylpyrrolidone; fluidizers or lubricants such as magnesium stearate, calcium stearate, talc, and synthetic aluminum silicate; colorants such as various pigments; and dissolution aids such as various surfactants; and the like.

The release rate of Compound I from the inner core of the coat-core tablet of the present invention is preferably higher than that from the outer layer portion. Although ingredients contained in the inner core are not particularly limited, the inner core is preferably a tablet containing Compound I and a disintegrant or a tablet containing Compound I and a gelling agent.

The disintegrants contained in the inner core are substances that disintegrate the inner core rapidly with a small volume of water to allow release of Compound I. The properties of disintegrating the inner core rapidly with a small volume of water refer to such properties that when an inner core (diameter 2 to 9 mm) is immersed in 1 mL of the 2nd fluid (pH 6.8) of the dissolution test of the Japanese Pharmacopoeia at 37° C., the inner core is disintegrated and dispersed within 10 minutes, preferably within 5 minutes. The properties that allow rapid release of a drug is, for example, such properties that when an inner core is subjected to the dissolution test by the paddle method of the Japanese Pharmacopoeia (test fluid: 900 mL of the 2nd fluid for the dissolution test of the Japanese Pharmacopoeia, temperature: 37° C., rotation number: 50 rotations/minute), the drug dissolution rate of 80% is achieved within 20 minutes, preferably within 15 minutes, more preferably within 10 minutes.

As the disintegrants, for example, carmellose, carmellose sodium, croscarmellose sodium, carmellose calcium, low-substituted hydroxypropylcellulose, starches such as carboxymethyl starch sodium, partly pregelatinized starch, pregelatinized starch, crospovidone, and the like may be used singly or in combination of two or more. Among the disintegrants described above, carboxymethyl starch sodium, partly pregelatinized starch, and croscarmellose sodium are preferable, and croscarmellose sodium is particularly preferable.

The inner core may contain the disintegrants in an amount in the range of 1 to 50% (w/w), preferably 1 to 30% (w/w), more preferably 1 to 20% (w/w) with respect to the weight of the inner core.

The inner core may contain, in addition to the disintegrants, as required, for example, sugars such as lactose, white sugar, glucose, fructose, trehalose, mannitol, sorbitol, xylitol, maltitol, and erythritol; starches such as wheat starch, corn starch, potato starch, partly pregelatinized starch, dextrin, hydroxypropyl starch, and carboxymethyl starch; celluloses such as microcrystalline cellulose; inorganic salts such as light anhydrous silicic acid, synthetic aluminum silicate, magnesium aluminometasilicate, and calcium phosphate; fats and oils such as paraffin, waxes, and higher fatty acids; binders such as hydroxypropylcellulose and polyvinylpyrrolidone; fluidizers or lubricants such as magnesium stearate, calcium stearate, talc, and synthetic aluminum silicate; colorants such as various pigments; dissolution aids such as various surfactants; and the like.

The gelling agent contained in the inner core is a substance that is gelled rapidly with a small amount of water. The properties of gelling rapidly with a small amount of digestive juice or water is, for example, such properties that when an inner core with a diameter of 6 mm (8R tablet), a thickness of 3.4 mm, and a mass of 100 mg is immersed in 1 mL of the 2nd fluid of the dissolution test of the Japanese Pharmacopoeia at 37° C., the inner core is completely gelled within 1 hour, preferably within 45 minutes; or when an inner core with a diameter of 5 mm (flat tablet), a thickness of 2.0 mm, and a mass of 50 mg is immersed in 1 mL of the 2nd fluid of the dissolution test of the Japanese Pharmacopoeia at 37° C., the inner core is completely gelled within 45 minutes, preferably with 30 minutes.

As the gelling agent, for example, the gel-forming water-soluble polymer used for the outer layer described above may be used. For example, hydroxypropylcellulose, hydroxypropylmethylcellulose, carmellose, carmellose sodium, methylcellulose, hydroxyethylcellulose, hydroxyethylmethylcellulose, pregelatinized starch, sodium alginate, gelatin, agar, tragacanth, xanthan gum, guar gum, gum arabic, carrageenan, carboxy vinyl polymer, polyethylene oxide, vinyl acetate povidone polymer matrix, polyvinyl alcohol, polyvinylpyrrolidone, Pullulan, sodium polyacrylate, polyoxyethylene(160)polyoxypropylene(30)glycol, and the like may be used singly or in combination of two or more. Among the gelling agents described above, sodium alginate, carmellose sodium, and carboxy vinyl polymer are preferable, and carboxy vinyl polymer is particularly preferable.

Carboxy vinyl polymer having a grade of viscosity of about 4,000 to 11,000 mPa·s or a grade of viscosity of about 29,400 to 39,400 mPa·s, as a viscosity grade defined by the viscosity test for carboxy vinyl polymer in accordance with the Japanese Pharmaceutical Excipients in terms of a 0.5% (w/v) aqueous solution at pH 7.5, may be used in the present invention, and it is preferable to use carboxy vinyl polymer of a grade of viscosity of about 29,400 to 39,400 mPa·s in terms of a 0.5% (w/v) aqueous solution at pH 7.5.

The inner core can contain the gelling agent in an amount in the range of 5 to 50% (w/w), preferably 5 to 40% (w/w), more preferably 5 to 30% (w/w) with respect to the weight of the inner core.

The inner core may contain, in addition to the gelling agents, as required, for example, sugars such as lactose, white sugar, glucose, fructose, trehalose, mannitol, sorbitol, xylitol, maltitol, and erythritol; starches such as wheat starch, corn starch, potato starch, partly pregelatinized starch, dextrin, hydroxypropyl starch, and carboxymethyl starch; celluloses such as microcrystalline cellulose; inorganic salts such as light anhydrous silicic acid, synthetic aluminum silicate, magnesium aluminometasilicate, and calcium phosphate; fats and oils such as paraffin, waxes, and higher fatty acids; disintegrants such as carmellose, carmellose sodium, croscarmellose sodium, carmellose calcium, starches, crospovidone, low-substituted hydroxypropylcellulose, microcrystalline cellulose, and powder cellulose; binders such as hydroxypropylcellulose and polyvinylpyrrolidone; fluidizers or lubricants such as magnesium stearate, calcium stearate, talc, and synthetic aluminum silicate; colorants such as various pigments; dissolution aids such as various surfactants; and the like.

The coat-core tablet comprising the inner core and the outer layer portion having the above compositions can be manufactured by the method known per se. The inner core may be obtained by conventional methods such as direct compression, granulation compression, or pill making. The outer layer portion may also be obtained by conventional methods such as wet granulation or dry granulation. The coat-core tablet may be manufactured by coating the inner core with the outer layer portion using a dry coater tablet press.

The diameter of the coat-core tablet of the present invention is not particularly limited, as far as the tablet can be administered orally and swallowed. The diameter of the coat-core tablet is generally in the range of 4 to 12 mm, and the diameter of the inner core is generally in the range of 2 to 9 mm.

The weight ratio of the outer layer portion to the inner layer of the coat-core tablet of the present invention is not particularly limited, although the ratio affects the thickness of the outer layer of the coat-core tablet formed. The weight ratio of the outer layer portion to the inner core can be selected from the range of 10/90 to 95/5, more preferably 20/80 to 95/5, further more preferably 30/70 to 95/5. The outer layer portion must have a certain thickness in order to avoid erosion of the inner core and the thickness is preferably 1 mm or more, and more preferably 1.5 mm or more.

Desirably, the final weight ratio of the outer layer to the inner core is determined by adjusting the thickness of the outer layer portion so that the dissolution rates of Compound I at a given time after the start of the dissolution test using modified paddle method of the dissolution test of the Japanese Pharmacopoeia with a stationary basket are:

5 to 30%, preferably 5 to 25%, more preferably 10 to 20% at 60 minutes,
25 to 55%, preferably 30 to 50%, more preferably 35 to 45% at 150 minutes,
70% or higher, preferably 80% or higher, more preferably 85% or higher at 240 minutes; or by adjusting the thickness of the outer layer portion so that the dissolution rates of Compound I by the dissolution test using modified paddle method of the dissolution test of the Japanese Pharmacopoeia with a stationary basket are:
5 to 30%, preferably 5 to 25%, more preferably 10 to 20% at 120 minutes,
25 to 55%, preferably 30 to 50%, more preferably 35 to 45% at 300 minutes,
70% or higher, preferably 80% or higher, more preferably 85% or higher at 480 minutes;
and the final weight ratio of the outer layer portion to the inner core is determined based on the thickness of the outer layer portion and the size and weight of the whole coat-core tablet.

The final weight ratio of Compound I contained in the outer layer portion to Compound I contained in the inner core in the coat-core tablet of the present invention is not particularly limited, although the ratio affects the amount of a drug absorbed in the upper digestive tract (the stomach and the small intestine) and in the lower digestive tract (the colon). The weight ratio can be determined appropriately depending on the weight and the size, the weight ratio of the outer layer portion to the inner core, the manufacturing processability of the outer layer portion and the inner core, and the like of the coat-core tablet.

The weight ratio of Compound I contained in the outer layer portion to Compound I contained in the inner core may be in the range of 5/95 to 95/5, preferably 10/90 to 95/5, further more preferably 15/85 to 95/5.

The weight ratio of Compound I contained in the outer layer portion to Compound I contained in the inner core is preferably adjusted so that the dissolution rates of Compound I at a given time after the start of the dissolution test using modified paddle method of the dissolution test of the Japanese Pharmacopoeia with a stationary basket are:

5 to 30%, preferably 5 to 25%, more preferably 10 to 20% at 60 minutes, 25 to 55%, preferably 30 to 50%, more preferably 35 to 45% at 150 minutes, 70% or higher, preferably 80% or higher, more preferably 85% or higher at 240 minutes; or so that the dissolution rates of Compound I by the dissolution test using modified paddle method of the dissolution test of the Japanese Pharmacopoeia with a stationary basket are:

5 to 30%, preferably 5 to 25%, more preferably 10 to 20% at 120 minutes, 25 to 55%, preferably 30 to 50%, more preferably 35 to 45% at 300 minutes, 70% or higher, preferably 80% or higher, more preferably 85% or higher at 480 minutes.

The characteristics of Compound I incorporated in the outer layer portion of the coat-core tablet of the present invention are not particularly limited; however, Compound I is preferably a drug having an average particle diameter as determined by an image analysis or by a particle size distribution measurement by using laser diffraction scattering (the median of a diameter in terms of volume conversion in the case of the measurement of particle size distribution by laser diffraction scattering) of 5.0 μm or more, further preferably of 8.0 μm or more. When the average particle diameter is smaller than 5.0 μm, the dissolution rate of Compound I is increased and the dissolution rate from the outer layer portion, especially that at a pH value higher than neutral becomes high, and as a result, it is sometimes difficult to release Compound I at a constant rate in the digestive tract in the region from the stomach to the lower part of the small intestine.

Further, the characteristics of Compound I incorporated in the inner core of the coat-core tablet of the present invention are not particularly limited, but Compound I is preferably finely milled crystals. The average particle diameter as determined by an image analysis or by a particle size distribution measurement by using laser diffraction scattering (the median of a diameter in terms of volume conversion in the case of the measurement of particle size distribution by laser diffraction scattering) is preferably 0.1 to 8.0 μm, more preferably 1.0 to 8.0 μm, further preferably 1.0 to 5.0 μm.

The inner core may be subjected to film coating before it is coated by the outer layer portion. The film coating agents include, for example, cellulose derivatives such as hydroxypropylcellulose and hydroxypropylmethylcellulose; water-soluble coating substrates such as polyvinyl alcohol and polyvinyl alcohol copolymer; cellulose derivative enteric coating substrates such as hydroxypropylmethylcellulose phthalate, hydroxypropylmethylcellulose acetate succinate, carboxymethylethylcellulose, and cellulose acetate phtalate; and enteric film coating substrates such as methacrylic acid copolymers and shellac.

The coat-core tablet may be further provided with a water-soluble film coating. As the film coating substrates, it is suitable to use hydroxypropylmethylcellulose preferably with a viscosity of 100 mPa·s or lower, particularly preferably with a viscosity of 17.5 mPa·s or lower in terms of a 2% (w/w) aqueous solution at 20° C. These film coating substrates may contain, as required, plasticizers such as polyethylene glycol, fluidizers such as talc, and colorants such as various pigments.

The drug applied to the coat-core tablet of the present invention includes, in addition to Compound I, xanthine oxidase inhibitors, and further 2-arylthiazole derivatives including Compound I. The amount of the drug contained in one coat-core tablet of the present invention is not particularly limited, but 5 mg to 200 mg, preferably 5 mg to 160 mg of the drug may be contained.

When the coat-core tablet of the present invention is administered to a human, Compound I preferably exhibits pharmacokinetics in the blood satisfying the following (a), (b), and (c):

(a) The plasma concentration of Compound I at the second peak in the plasma concentration-time profile is 0.2 μg/mL or higher, or the plasma concentration at 24 hours after administration is 0.05 μg/mL or higher, in 80 mg dose of Compound I;

(b) The maximum blood concentration (Cmax) of Compound I is less than 2.0 μg/mL. More preferably, the maximum blood concentration (Cmax) is 0.8 to 2.0 μg/mL, or the maximum blood concentration (Cmax) is 0.3 to 0.8 μg/mL, in 80 mg dose of Compound I;

(c) The ratio of the area under the plasma concentration-time curve from time zero to time infinity (AUC∞ (ng·hr/mL)) to the maximum blood concentration (Cmax (ng/mL)), AUC∞:Cmax, is 5.0:1 to 20:1. More preferably, the ratio of the area under the plasma concentration-time curve from time zero to time infinity (AUC∞ (ng·hr/mL)) to the maximum blood concentration (Cmax (ng/mL)), AUC∞:Cmax, is 5.0:1 to 7.5:1, or the ratio of the area under the plasma concentration-time curve from time zero to time infinity (AUC∞ (ng·hr/mL)) to the maximum blood concentration (Cmax (ng/mL)), AUC∞:Cmax, is 7.5:1 to 15.0:1, in 80 mg dose of Compound I.

EXAMPLES

Examples of the present invention will be described below. The present invention is not limited by the following Examples, however.

Here, Compound I, incorporated in the outer layer portion, having an average particle diameter (the median of a diameter calculated by volume conversion in the measurement of particle size distribution by laser diffraction scattering) of 8.0 μm or more was used, and Compound I, incorporated in the inner core, having an average particle diameter (the median of a diameter calculated by volume conversion in the measurement of particle size distribution by laser diffraction scattering) of 1.0 to 5.0 μm was used. METOLOSE 90SH-100SR, METOLOSE 90SH-4000SR, and METOLOSE 90SH-100000SR are the trade names of Shin-Etsu Chemical Co., Ltd., and refer to hydroxypropylmethylcellulose 2208 of viscosity grades of about 80 to about 120 mPa·s, about 3,000 to about 5,600 mPa·s, and about 75,000 to about 140,000 mPa·s, respectively, in terms of a 2% (w/w) aqueous solution at 20° C. METOLOSE 60SH-50 and TC-5R are the trade names of Shin-Etsu Chemical Co., Ltd., and refer to hydroxypropylmethylcellulose 2910 of viscosity grades of about 40 to about 60 mPa·s and about 5.2 to about 7.0 mPa·s, respectively, in terms of a 2% (w/w) aqueous solution at 20° C. Eudragit RSPO is the trade name of Evonik Degussa Japan Co., Ltd., and refers to an aminoalkyl methacrylate copolymer RS. Opadry II Green is the trade name of Colorcon Japan LLC., and is a premixed additive to which an additive for water-soluble film coating is mixed in advance. As hydroxypropylcellulose, hydroxypropylcelluloses of Nippon Soda Co., Ltd., of viscosity grades of about 3.0 to about 5.9 mPa·s (HPC-SL), about 6.0 to about 10.0 mPa·s (HPC-L), and about 150 to about 400 mPa·s (HPC-M) in terms of 2% (w/w) aqueous solution at 20° C. were used.

Example 1

TABLE 1

| Compound I | 247.5 g |
|---|---|
| (Average particle diameter: 1.5 μm) | |
| Lactose monohydrate | 577.2 g |
| Partly pregelatinized starch | 150.5 g |
| HPC-SL | 24.7 g |
| Food Blue No. 1 | 0.1 g |

The above-described raw materials were mixed homogeneously, and the mixture was granulated by fluidized bed granulation, then dried, and subjected to particle size regulation. To 97.0% (w/w) of the powder obtained, 2.0% (w/w) of croscarmellose sodium and 1.0% (w/w) of magnesium stearate were added and mixed. The mixture was subjected to tabletting by a rotary tabletting machine (HT-AP6SS-U; Hata Iron Works Co., Ltd.) under a compression force of about 550 kg to obtain inner cores (diameter: 6 mm, thickness: 3.2 mm), each tablet having a mass of 100 mg.

TABLE 2

| Compound I | 140 g |
|---|---|
| (Average particle diameter: 13.7 μm) | |
| METOLOSE 90SH-100SR | 400 g |
| Lactose monohydrate | 435 g |
| HPC-SL | 25 g |

The above-described raw materials were mixed, and the mixture was granulated by wet agitation granulation, then dried, and subjected to particle size regulation. To the powder obtained, 0.5% (w/w) of magnesium stearate was added and mixed. This composition was used for the outer layer portion, and tabletted together with the inner core previously prepared by a dry coater tablet press (Libra 45DC; Kikusui Seisakusho Ltd.) under a compression force of about 1 ton to obtain coat-core tablets (diameter: 10 mm, thickness: 6.5 mm), each tablet having a mass of 502 mg and containing 80 mg of Compound I.

Example 2

TABLE 3

| Compound I | 240 g |
|---|---|
| (Average particle diameter: 1.5 μm) | |
| Carboxy vinyl polymer | 100 g |
| Lactose monohydrate | 634.9 g |
| HPC-SL | 25 g |
| Food Blue No. 1 | 0.1 g |

The above-described raw materials were mixed homogenously, granulated by wet agitation granulation, then dried, and subjected to particle size regulation. To the powder obtained, 0.5% (w/w) of magnesium stearate was added and mixed. The mixture was tabletted by a rotary tabletting machine (HT-AP6SS-U; Hata Iron Works Co., Ltd.) under a compression force of about 350 kg to obtain inner cores (diameter: 6 mm, thickness: 3.4 mm), each tablet having a mass of 100.5 mg.

TABLE 4

| Compound I | 140 g |
|---|---|
| (Average particle diameter: 13.7 μm) | |
| METOLOSE 90SH-100SR | 400 g |
| Lactose monohydrate | 435 g |
| HPC-SL | 25 g |

The above-described raw materials were mixed homogenously, granulated by wet agitation granulation, then dried, and subjected to particle size regulation. To the powder obtained, 0.5% (w/w) of magnesium stearate was added and mixed. This composition was used for the outer layer portion and tabletted together with the inner core previously prepared by a dry coater tablet press (Libra 45DC; Kikusui Seisakusho Ltd.) under a compression force of about 1 ton to obtain coat-core tablets (diameter: 10 mm, thickness: 6.5 mm), each tablet containing 80 mg of Compound I and having a mass of 502.5 mg.

Example 3

TABLE 5

| Compound I | 247.5 g |
|---|---|
| (Average particle diameter: 1.5 μm) | |
| Lactose monohydrate | 577.2 g |
| Partly pregelatinized starch | 150.5 g |
| HPC-SL | 24.7 g |
| Food Blue No. 1 | 0.1 g |

The above-described raw materials were mixed homogenously, granulated by fluidized bed granulation, then dried, and subjected to particle size regulation. To 97.0% (w/w) of the powder obtained, 2.0% (w/w) of croscarmellose sodium and 1.0% (w/w) of magnesium stearate were added and mixed. The mixture was tabletted by a rotary tabletting machine (HT-AP6SS-U; Hata Iron Works Co., Ltd.) under a compression force of about 550 kg to obtain inner cores (diameter: 6 mm, thickness: 3.2 mm), each tablet having a mass of 100 mg.

TABLE 6

| Compound I | 140 g |
|---|---|
| (Average particle diameter: 13.7 μm) | |
| METOLOSE 90SH-100SR | 200 g |
| METOLOSE 90SH-4000SR | 200 g |
| Lactose monohydrate | 435 g |
| HPC-SL | 25 g |

The above-described raw materials were mixed homogenously and granulated by wet agitation granulation, then dried, and subjected to particle size regulation. To the powder obtained, 0.5% (w/w) of magnesium stearate was added and mixed. This composition was used for the outer layer portion and tabletted together with the inner core previously prepared by a dry coater tablet press (Libra 45DC; Kikusui Seisakusho Ltd.) under a compression force of about 1 ton to obtain coat-core tablets (diameter: 10 mm, thickness: 6.5 mm), each tablet containing 80 mg of Compound I and having a mass of 502 mg.

Example 4

TABLE 7

| | |
|---|---|
| Compound I | 240 g |
| (Average particle diameter: 1.5 μm) | |
| Carboxy vinyl polymer | 100 g |
| Lactose monohydrate | 634.9 g |
| HPC-SL | 25 g |
| Food Blue No. 1 | 0.1 g |

The above-described raw materials were mixed homogenously, granulated by wet agitation granulation, then dried, and subjected to particle size regulation. To the powder obtained, 0.5% (w/w) of magnesium stearate was added and mixed. The mixture was tabletted by a rotary tabletting machine (HT-AP6SS-U; Hata Iron Works Co., Ltd.) under a compression force of about 350 kg to obtain inner cores (diameter: 6 mm, thickness: 3.4 mm), each tablet having a mass of 100.5 mg.

TABLE 8

| | |
|---|---|
| Compound I | 140 g |
| (Average particle diameter: 13.7 μm) | |
| METOLOSE 90SH-100SR | 200 g |
| METOLOSE 90SH-4000SR | 200 g |
| Lactose monohydrate | 435 g |
| HPC-SL | 25 g |

The above-described raw materials were mixed homogenously, granulated by wet agitation granulation, then dried, and subjected to particle size regulation. To the powder obtained, 0.5% (w/w) of magnesium stearate was added and mixed. This composition was used for the outer layer portion and tabletted together with the inner core previously prepared by a dry coater tablet press (Libra 45DC; Kikusui Seisakusho Ltd.) under a compression force of about 1 ton to obtain coat-core tablets (diameter: 10 mm, thickness: 6.5 mm), each tablet containing 80 mg of Compound I and having a mass of 502.5 mg.

Comparative Example 1

TABLE 9

| | |
|---|---|
| Compound I | 80 mg |
| Lactose monohydrate | 76.5 mg |
| Microcrystalline cellulose (Avicel PH101) | 129 mg |
| Microcrystalline cellulose (Avicel PH102) | 172.5 mg |
| Hydroxypropylcellulose | 12 mg |
| Croscarmellose sodium | 25 mg |
| Magnesium stearate | 2.5 mg |
| Silicon dioxide | 2.5 mg |
| Opadry II Green | 20 mg |
| Total of a tablet | 520 mg |

Compound I, lactose monohydrate, microcrystalline cellulose, hydroxypropylcellulose, and croscarmellose sodium shown in Table 9 were mixed homogenously, granulated by wet agitation granulation, then dried, and subjected to particle size regulation. To the powder obtained, magnesium stearate and silicon dioxide were added and mixed, and the mixture was subjected to compression molding with oval-shaped punches and dies to obtain tablets, each tablet having a weight of 500 mg. This tablet was coated with Opadry II to obtain a coated tablet of 520 mg.

Test Example 1

The coat-core tablet of Example 1 was subjected to a dissolution test using modified paddle method of the dissolution test of the Japanese Pharmacopoeia with a stationary basket. The conditions of the test were as follows:
Test fluid: 900 mL of diluted McIlvaine buffer at pH 6.0
Temperature: 37° C.
Number of rotation: 200 rotations/minute
Stationary basket: A 40-mesh basket was fixed at the position in the middle between the surface of a test fluid and the bottom of the vessel and about 23 mm from the side wall of a vessel of the dissolution test fluid.

As shown in FIG. 1, the dissolution profile was confirmed in which Compound I was dissolved from the outer layer portion at a constant rate up to 3 to 4 hours after the start of the test and then the inner core was exposed and dissolution of Compound I from the inner core was started.

Test Example 2

Figure 2:
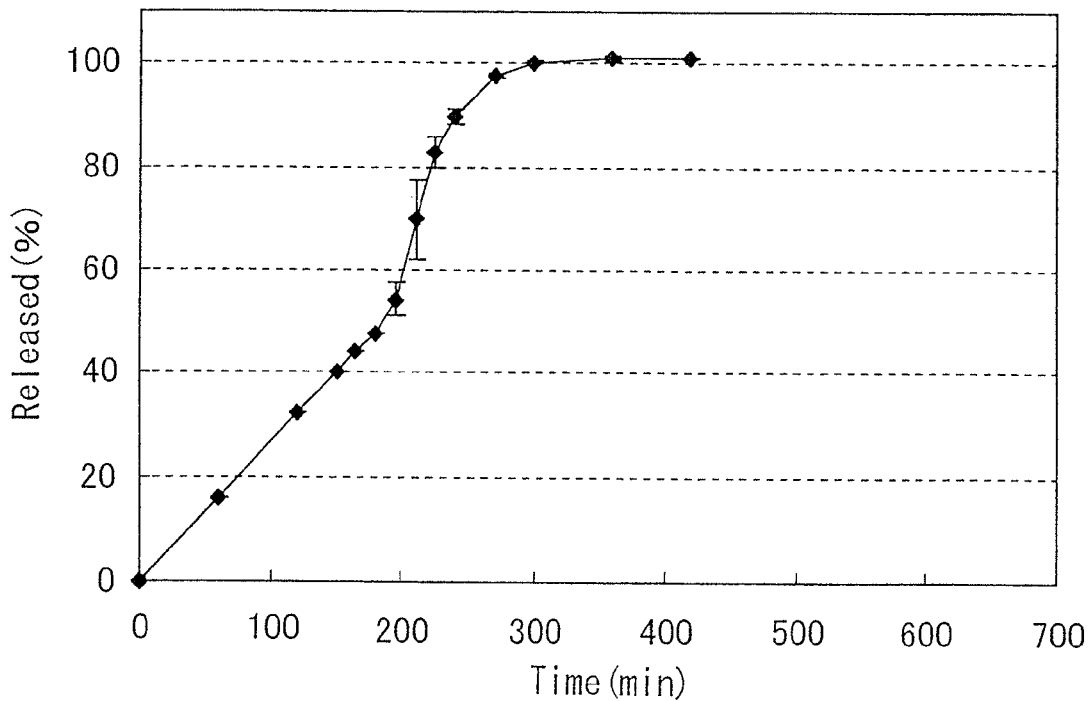
FIG. 2 shows the results of the dissolution test of Example 2, Test Example 2 (average of N=3).

The coat-core tablet of Example 2 was subjected to a dissolution test using modified paddle method of the dissolution test of the Japanese Pharmacopoeia with a stationary basket. The conditions of the test were as follows:
Test fluid: 900 mL of diluted McIlvaine buffer at pH 6.0
Temperature: 37° C.
Number of rotation: 200 rotations/minute
Stationary basket: A 40-mesh basket was fixed at the position in the middle between the surface of s test fluid and the bottom of the vessel and about 23 mm from the side wall of a vessel of the dissolution test fluid. As shown in FIG. 2. the dissolution profile was confirmed in which Compound I was dissolved from the outer layer portion at a constant rate up to 3 to 4 hours after the start of the test and then the inner core was exposed and dissolution of Compound I from the inner core was started

Test Example 3

The coat-core tablet of Example 3 was subjected to a dissolution test using modified paddle method of the dissolution test of the Japanese Pharmacopoeia with a stationary basket. The conditions of the test were as follows:
Test fluid: 900 mL of diluted McIlvaine buffer at pH 6.0
Temperature: 37° C.
Number of rotation: 200 rotations/minute
Stationary basket: A 40-mesh basket was fixed at the position in the middle between the surface of a test fluid and the bottom of a vessel and about 23 mm from the side wall of a vessel of the dissolution test fluid.

Figure 3:
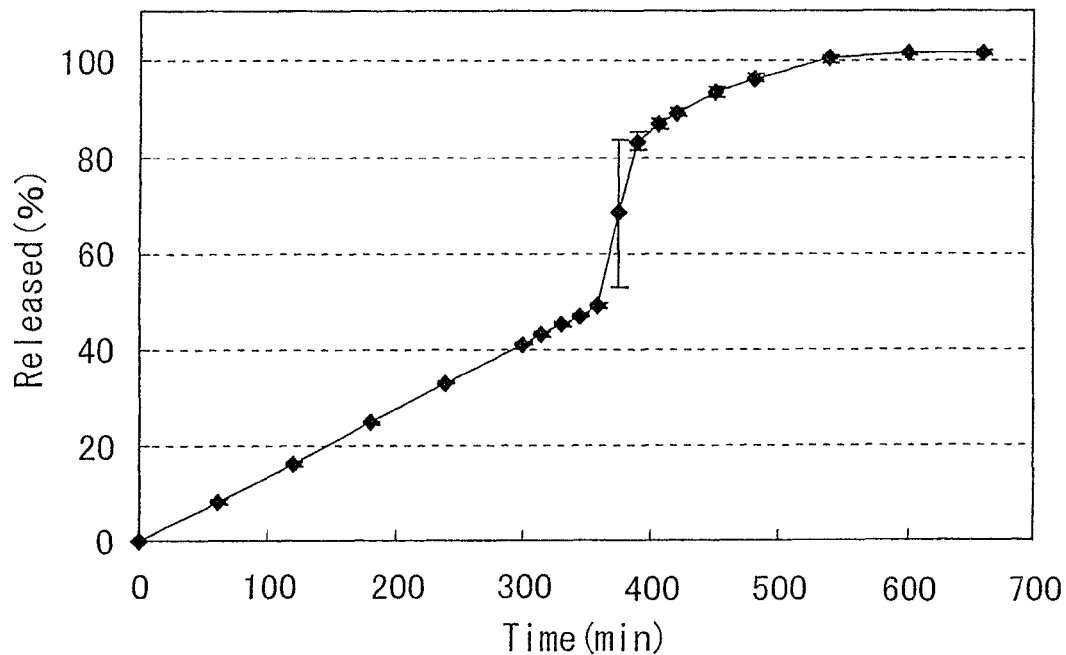
FIG. 3 shows the results of the dissolution test of Example 3, Test Example 3 (average of N=3).

As shown in FIG. 3, the dissolution profile was confirmed in which Compound I was dissolved from the outer layer portion at a constant rate up to 6 to 7 hours after the start of the test and then the inner core was exposed and dissolution of Compound I from the inner core was started.

Test Example 4

The coat-core tablet of Example 4 was subjected to a dissolution test using modified paddle method of the dissolution test of the Japanese Pharmacopoeia with a stationary basket.

The conditions of the test were as follows:
Test fluid: 900 mL of diluted McIlvaine buffer at pH 6.0
Temperature: 37° C.
Number of rotation: 200 rotations/minute
Stationary basket: A 40-mesh basket was fixed at the position in the middle between the surface of a test fluid and the bottom of a vessel and about 23 mm from the side wall of a vessel of the dissolution test fluid.

Figure 4:
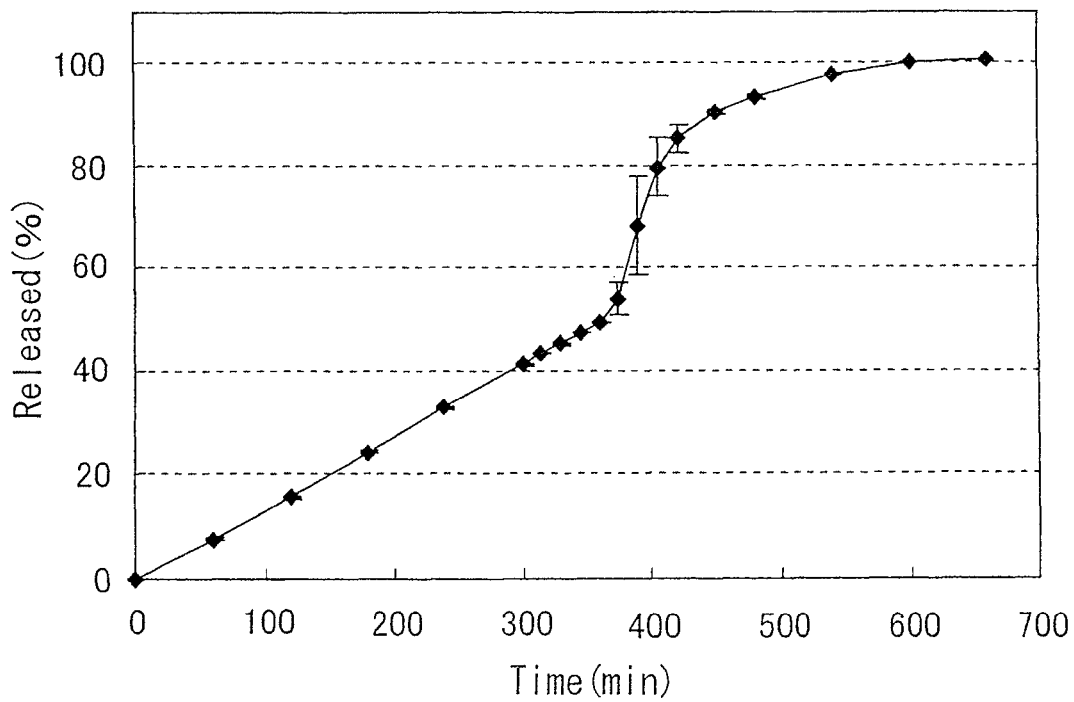
FIG. 4 shows the results of the dissolution test of Example 4, Test Example 4 (average of N=3).

As shown in FIG. 4, the dissolution profile was confirmed in which Compound I was dissolved from the outer layer portion at a constant rate by 6 to 7 hours after the start of the test and then the inner core was exposed and dissolution of Compound I from the inner core was started.

Test Example 5

TABLE 10

| Compound I | 247.5 g |
|---|---|
| (Average particle diameter: 1.5 μm) | |
| Lactose monohydrate | 577.2 g |
| Partly pregelatinized starch | 150.5 g |
| HPC-SL | 24.7 g |
| Food Blue No. 1 | 0.1 g |

The above-described raw materials were mixed homogenously, granulated by fluidized bed granulation, then dried, and subjected to particle size regulation. To 97.0% (w/w) of the powder obtained, 2.0% (w/w) of croscarmellose sodium and 1.0% (w/w) of magnesium stearate were added and mixed. The mixture was tabletted by a rotary tabletting machine (HT-AP6SS-U; Hata Iron Works Co., Ltd.) under a compression force of about 550 kg to obtain inner cores (diameter: 6 mm, thickness: 3.2 mm), each tablet having a mass of 100 mg.

Figure 5:
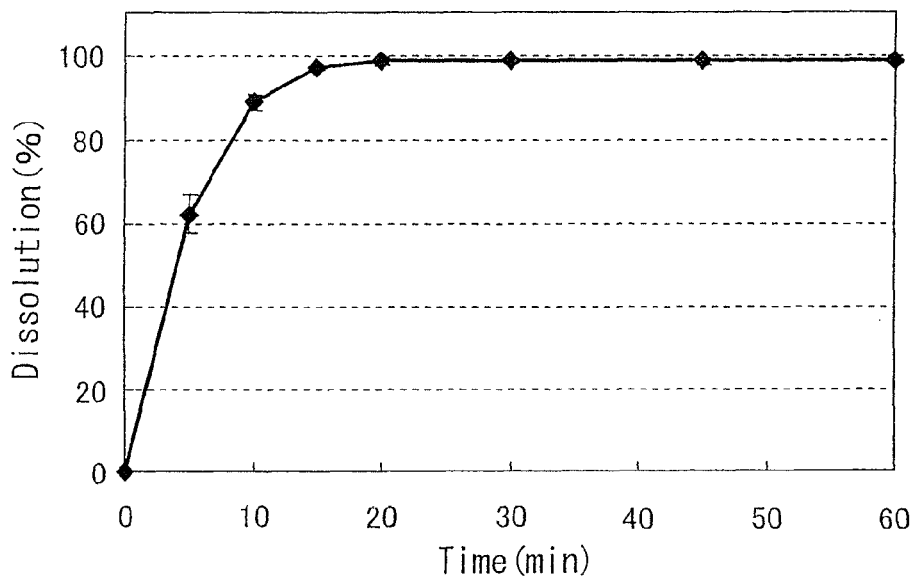
FIG. 5 shows the results of the dissolution test in Test Example 5 (average of N=3).

The inner core was subjected to a dissolution test by the paddle method of the dissolution test of the Japanese Pharmacopoeia. The conditions of the test were as follows:
Test fluid: 900 mL of the 2nd fluid for dissolution test of the Japanese Pharmacopoeia
Temperature: 37° C.
Number of rotation: 50 rotations/minute As shown in FIG. 5, it was confirmed that 80% or more of Compound I was dissolved within 10 minutes after the start of the test.

Test Example 6

TABLE 11

| Compound I | 240 g |
|---|---|
| (Average particle diameter: 1.5 μm) | |
| Carboxy vinyl polymer | 100 g |
| Lactose monohydrate | 634.9 g |
| HPC-SL | 25 g |
| Food Blue No. 1 | 0.1 g |

The above-described raw materials were mixed homogenously, granulated by wet agitation granulation, then dried, and subjected to particle size regulation. To the powder obtained, 0.5% (w/w) of magnesium stearate was added and mixed. The mixture was tabletted by a rotary tabletting machine (HT-AP6SS-U; Hata Iron Works Co., Ltd.) under a compression force of 350 kg to obtain inner core 1 having the size shown below. Inner core 1: A tablet having a mass of 100 mg, a diameter of 6 mm 8R, and a thickness of 3.4 mm In addition, inner core 2 having the size shown below was manufactured using a simple tablet forming machine (hand press) under a compression force of 400 kg. Inner core 2: A tablet having a mass of 50 mg, with a form of plane disk having a diameter of 5 mm and a thickness of 2.0 mm.

To a 12-well plate for cell culture, 1 mL/well of a test fluid (the 2nd fluid for dissolution test of the Japanese Pharmacopoeia) at 37° C. was charged, and one tablet of the inner core 1 or inner core 2 was placed in each well and incubated at 37° C. The inner cores were removed at predetermined timings and cut by a cutter to obtain a cross section, which was observed visually for gellation.

It was confirmed that the inner cores 1 and 2 were completely gelled at 40 and 30 minutes, respectively, after the test fluid was added.

Test Example 7

TABLE 12

| | Outer layer portion tablet 1 | Outer layer portion tablet 2 | Outer layer portion tablet 3 | Outer layer portion tablet 4 |
|---|---|---|---|---|
| Compound I (Average particle diameter: 13.7 μm) | 1.4 g | 1.4 g | 1.4 g | 1.4 g |
| METOLOSE 90SH-100SR | 4.0 g | — | 2.0 g | — |
| METOLOSE 90SH-4000SR | — | 1.5 g | 2.0 g | 0.75 g |
| METOLOSE 90SH-100000SR | — | — | — | 0.75 g |
| Lactose monohydrate | 4.35 g | 6.85 g | 4.35 g | 6.85 g |
| HPC-SL | 0.25 g | 0.25 g | 0.25 g | 0.25 g |

The above-listed raw materials were mixed homogenously, granulated by wet agitation granulation, then dried, and subjected to particle size regulation. To the powder obtained, 0.5% (w/w) of magnesium stearate was added and mixed. 150 mg of this composition was subjected to compression molding using a simple tablet forming machine (hand press) to obtain a tablet having a diameter of 7 mm and a hardness of about 6 kgf and containing only the outer layer portion ingredients.

These outer layer portion tablets 1 to 4 were subjected to a disintegration test in accordance with the disintegration test of the Japanese Pharmacopoeia. The conditions of the test were as follows:
Test Fluid:
900 mL of diluted McIlvaine buffer (pH 6.0), or
900 mL of the 2nd fluid for dissolution test of the Japanese Pharmacopoeia (pH 6.8), or
900 mL of phosphate buffer (pH 7.4)
Temperature: 37° C.
Number of strokes: 30 strokes/minute One table was placed in a sinker for the dissolution test of the Japanese Pharmacopoeia and charged in a disintegration test machine.

TABLE 13

| | Placebo tablet 1 | Placebo tablet 2 | Placebo tablet 3 | Placebo tablet 4 |
|---|---|---|---|---|
| METOLOSE 90SH-100SR | 4.0 g | — | 2.0 g | — |

TABLE 13-continued

|  | Placebo tablet 1 | Placebo tablet 2 | Placebo tablet 3 | Placebo tablet 4 |
| --- | --- | --- | --- | --- |
| METOLOSE 90SH-4000SR | — | 1.5 g | 2.0 g | 0.75 g |
| METOLOSE 90SH-100000SR | — | — | — | 0.75 g |
| Lactose monohydrate | 5.75 g | 8.25 g | 5.75 g | 8.25 g |
| HPC-SL | 0.25 g | 0.25 g | 0.25 g | 0.25 g |

The above-listed raw materials were mixed homogenously, granulated by wet agitation granulation, then dried, and subjected to particle size regulation. To the powder obtained, 0.5% (w/w) of magnesium stearate was added and mixed. 150 mg of this composition was subjected to compression molding using a simple tablet forming machine (hand press) to obtain a tablet having a diameter of 7 mm and a hardness of about 6 kgf and containing only the outer layer portion ingredients.

These placebo tablets 1 to 4 were subjected to a disintegration test in accordance with the dissolution test of the Japanese Pharmacopoeia. The conditions of the test were as follows:
Test Fluid:
900 mL of diluted McIlvaine buffer (pH 6.0), or
900 mL of the 2nd fluid for dissolution test of the Japanese Pharmacopoeia (pH 6.8), or
900 mL of phosphate buffer (pH 7.4)
Temperature: 37° C.
Number of strokes: 30 strokes/minute One table was placed in a sinker for the dissolution test of the Japanese Pharmacopoeia and charged in a disintegration test machine.

Figure 6:
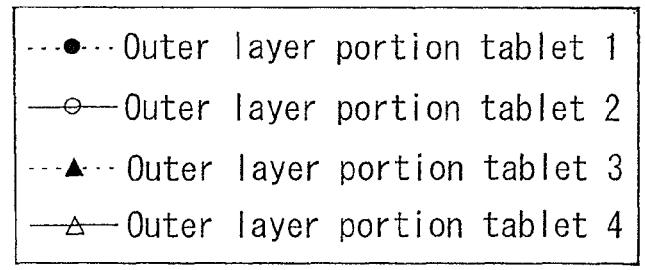
FIG. 6 shows the results of the disintegration test in Test Example 7 (average of N=3).
Figure 6:
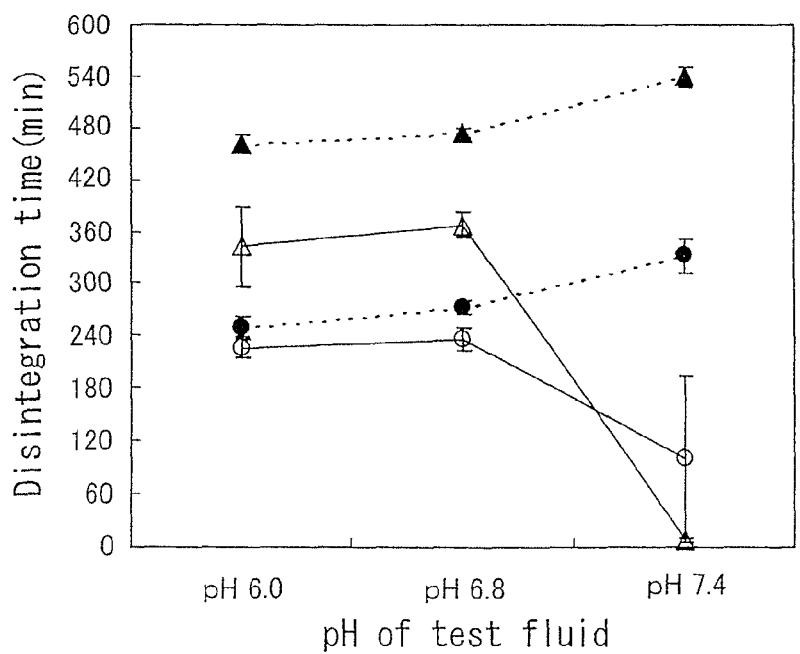
Figure 7:
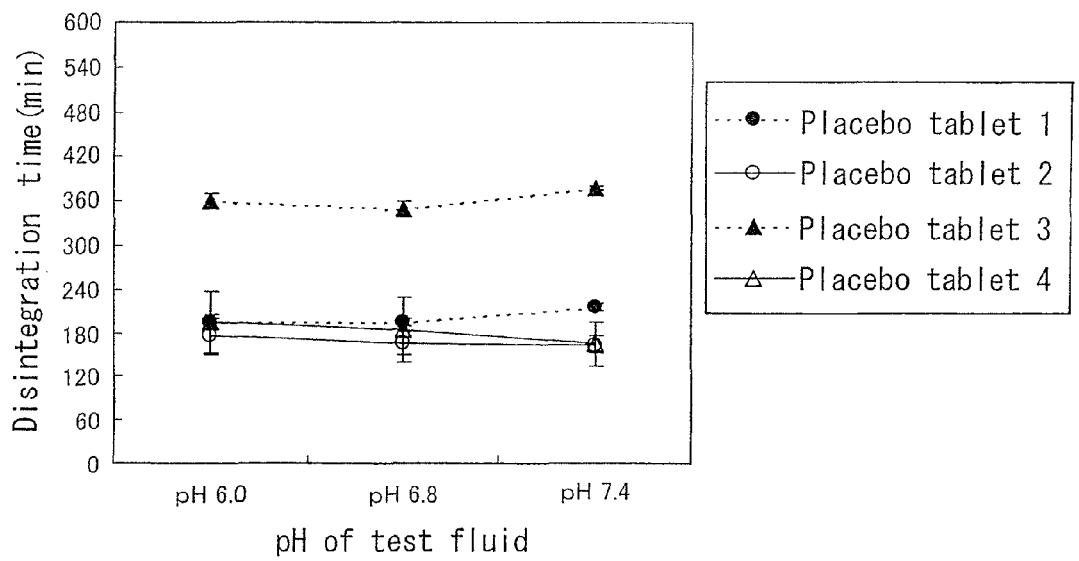
FIG. 7 shows the results of the disintegration test in Test Example 7 (average of N=3).

The results show that the disintegration times of the outer layer portion tablet 2 and the outer layer portion tablet 4 were markedly influenced by pH, and the disintegration time was short at pH 7.4 and varied among the tablets as shown in FIG. 6. As shown in FIG. 7, on the other hand, the disintegration times of the placebo tablets were not influenced by pH for any of the formulations. From the above results, it was confirmed that, when the content of hydroxypropylmethylcellulose in the outer layer portion containing Compound I was low, the disintegration of the tablet was faster, the sustainability of the tablet was lost and the variation of disintegration among the tablets became larger with the increase in pH.

Test Example 8

TABLE 14

|  | Outer layer portion tablet 5 | Outer layer portion tablet 6 | Outer layer portion tablet 7 |
| --- | --- | --- | --- |
| Compound I (Average particle diameter: 13.7 μm) | 1.4 g | 1.4 g | 1.4 g |
| METOLOSE 90SH-100SR | — | — | 6.0 g |
| METOLOSE 90SH-4000SR | 2.0 g | 2.5 g | — |
| Lactose monohydrate | 6.35 g | 5.85 g | 2.35 g |
| HPC-SL | 0.25 g | 0.25 g | 0.25 g |

The above-listed raw materials were mixed homogenously, granulated by wet agitation granulation, then dried, and subjected to particle size regulation. To the powder obtained, 0.5% (w/w) of magnesium stearate was added and mixed. 150 mg of this composition was subjected to compression molding using a simple tablet forming machine (hand press) to obtain a tablet having a diameter of 7 mm and a hardness of about 6 kgf and containing only the outer layer portion ingredients.

These outer layer portion tablets 5 to 7 were subjected to a disintegration test in accordance with the disintegration test of the Japanese Pharmacopoeia. The conditions of the test were as follows:
Test Fluid:
900 mL of diluted McIlvaine buffer (pH 6.0), or
900 mL of the 2nd fluid for dissolution test of the Japanese Pharmacopoeia (pH 6.8), or
900 mL of phosphate buffer (pH 7.4)
Temperature: 37° C.
Number of strokes: 30 strokes/minute One table was placed in a sinker for the dissolution test of the Japanese Pharmacopoeia and charged in a disintegration test machine.

Figure 8:
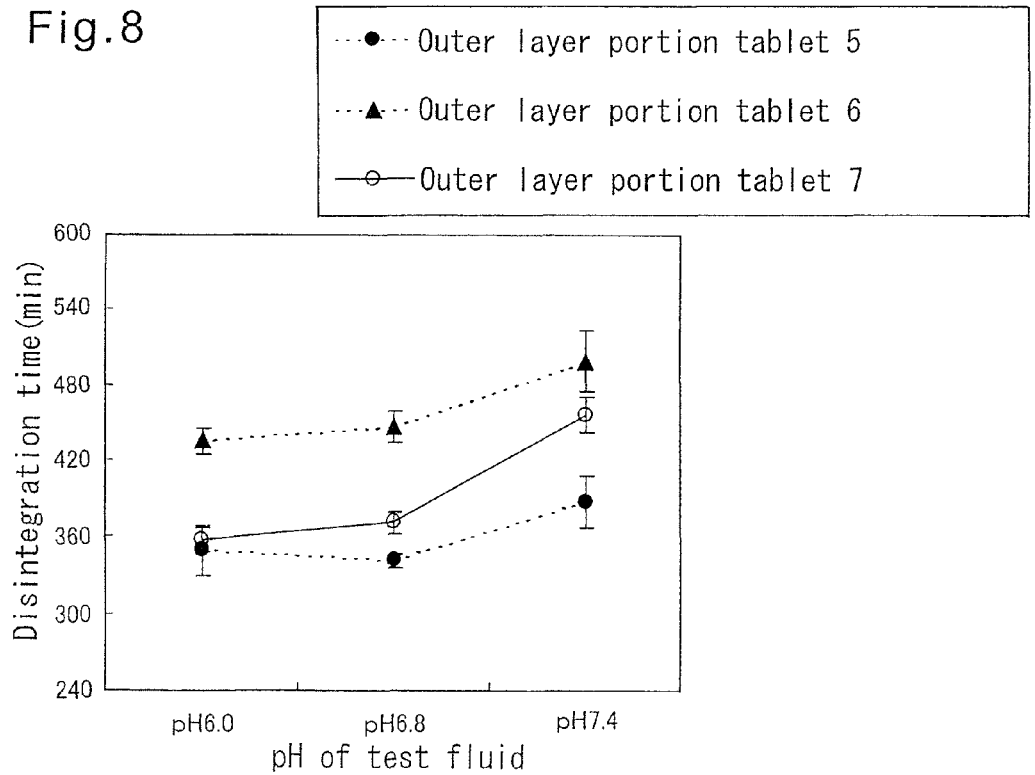
FIG. 8 shows the results of the disintegration test in Test Example 8 (average of N=3).

The results show that the disintegration times of the outer layer portion tablet 5 and the outer layer portion tablet 6 were not influenced by pH. However, the disintegration time of the outer layer portion tablet 7 had a tendency to be longer at pH 7.4 than that of the outer layer portion tablet 5 and 6 at pH 7.4 as shown in FIG. 8.

Test Example 9

TABLE 15

|  | Outer layer portion tablet 8 | Outer layer portion tablet 9 | Outer layer portion tablet 10 | Outer layer portion tablet 11 |
| --- | --- | --- | --- | --- |
| Compound I (Average particle diameter: 13.7 μm) | 1.4 g | 1.4 g | 1.4 g | 1.4 g |
| METOLOSE 90SH-100SR | 4.0 g | — | — | — |
| METOLOSE 90SH-4000SR | — | 1.5 g | — | — |
| METOLOSE 60SH-50 | — | — | 6.0 g | — |
| TC-5R | — | — | — | 6.0 g |
| Lactose monohydrate | 4.35 g | 6.85 g | 2.35 g | 2.35 g |
| HPC-SL | 0.25 g | 0.25 g | 0.25 g | 0.25 g |

Figure 9:
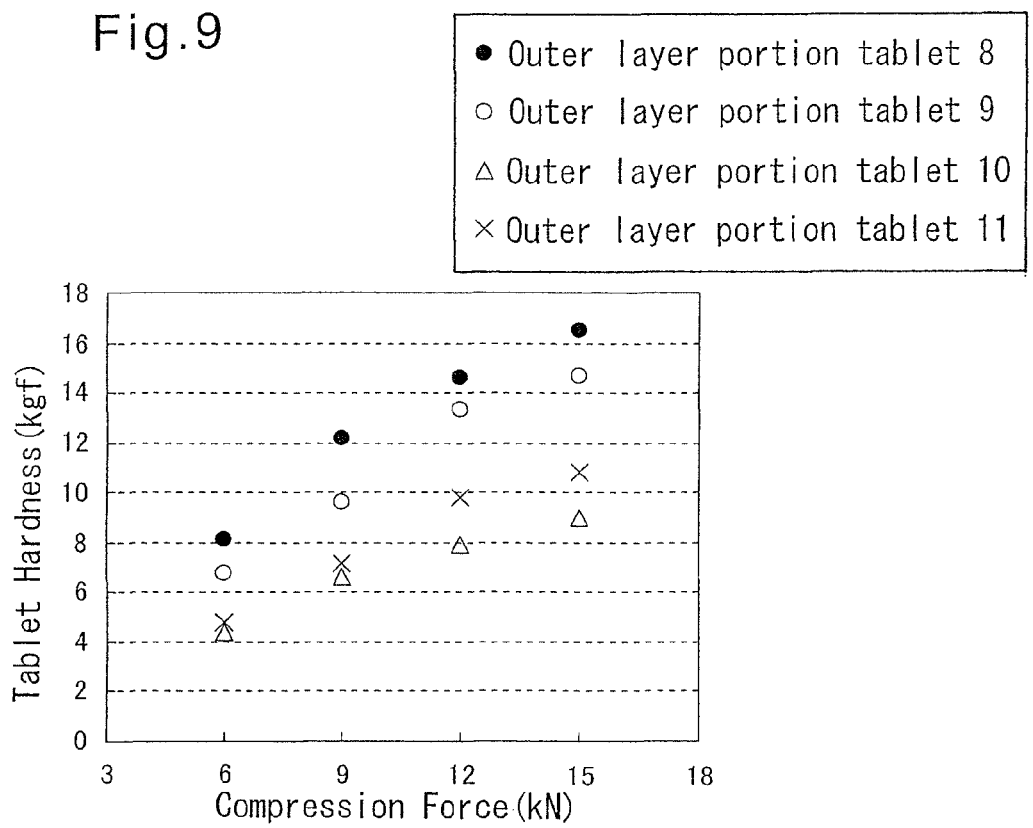
FIG. 9 shows the relationship between compression force and tablet hardness in Test Example 9.

The above-listed raw materials were mixed homogenously, granulated by wet agitation granulation, then dried, and subjected to particle size regulation. To the powder obtained, 0.5% (w/w) of magnesium stearate was added and mixed. 502 mg of this composition was subjected to compression molding by a simple tablet forming machine (hand press) with a compression force shown below to obtain a tablet having a diameter of 10 mm and containing only the outer layer portion ingredients. Hardness of the tablets obtained was measured using a tablet hardness tester (Toyama Sangyo Co., Ltd.):
Compression forces: 6 kN, 9 kN, 12 kN, and 15 kN As a result, as shown in FIG. 9, the hardness was the highest for the outer layer portion tablet 8 containing 40% of hydroxypropylmethylcellulose, followed by the outer layer portion tablet 9 containing 15% of hydroxypropylmethylcellulose, and the lowest for the outer layer portion tablet 10 and the outer layer portion tablet 11 each containing 60% of hydroxypropylmethylcellulose. From the above results, it was confirmed that the outer layer portion tablet containing 40% of hydroxypropylmethylcellulose had better compression moldability than the outer layer portion tablets having hydroxypropylmethylcellulose contents other than 40%.

Test Example 10

TABLE 16

|  | Outer layer portion tablet 12 | Outer layer portion tablet 13 |
| --- | --- | --- |
| Compound I (Average particle diameter: 13.7 μm) | 140 g | 1.4 g |
| METOLOSE 90SH-100SR | 400 g | — |
| Eudragit RSPO | — | 2.0 g |
| HPC-M | — | 1.0 g |
| HPC-L | — | 3.0 g |
| Lactose monohydrate | 435 g | 2.35 g |
| HPC-SL | 25 g | 0.25 g |

The above-listed raw materials were mixed homogenously, granulated by wet agitation granulation, then dried, and subjected to particle size regulation. To the powder obtained, 0.5% (w/w) of magnesium stearate was added and mixed. 502 mg of this composition was subjected to compression molding by a simple tablet forming machine (hand press) to obtain a tablet having a diameter of 10 mm and a hardness of about 9 kgf and containing only the outer layer portion ingredients.

The outer layer portion tablets 12 and 13 were subjected to a dissolution test using modified paddle method of the dissolution test of the Japanese Pharmacopoeia with a stationary basket. The conditions of the test were as follows:
Test fluid: 900 mL of the 2nd fluid for dissolution test (pH 6.8) of the Japanese Pharmacopoeia
Temperature: 37° C.
Number of rotation: 50 rotations/minute or 200 rotations/minute
Stationary basket: An 8-mesh basket was fixed at the position 23 mm from the side wall of a vessel of a dissolution test fluid, with the bottom of a basket being 1 cm from the upper side of the paddle.

Figure 10:
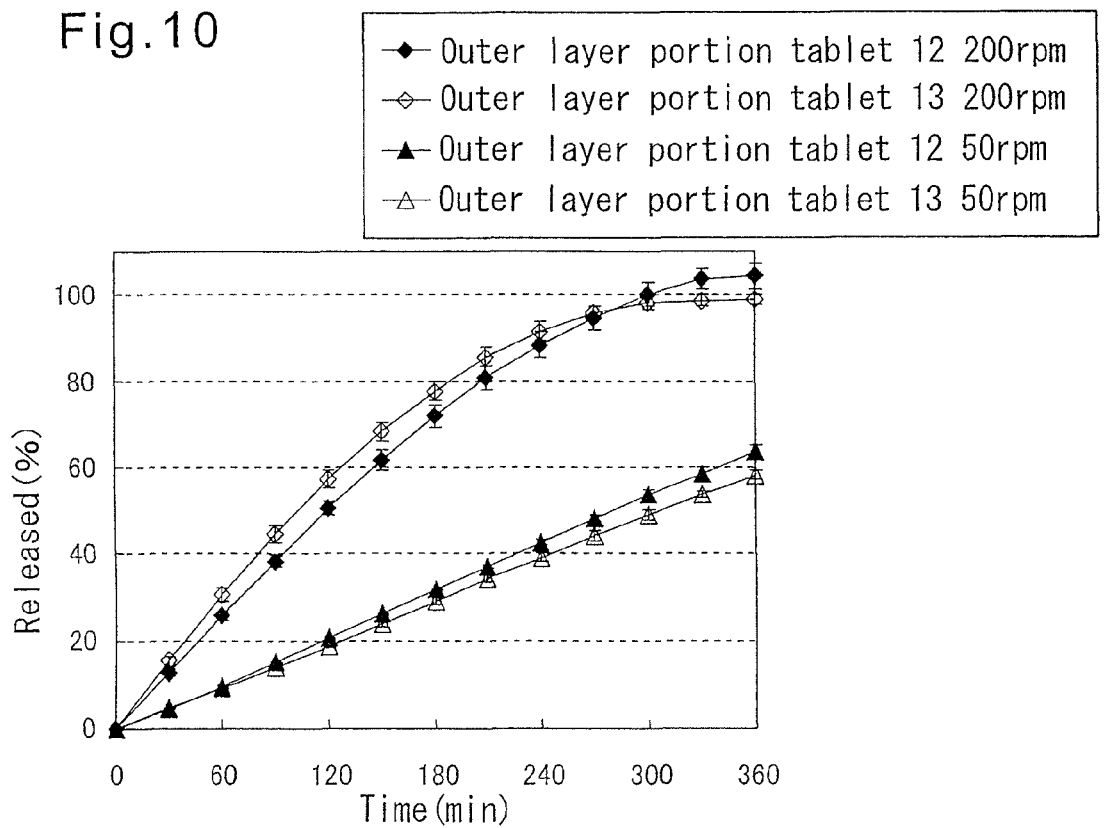
FIG. 10 shows the results of the dissolution test in Test Example 10 (average of N=3).

As a result, as shown in FIG. 10, the dissolution rate of compound I from the outer layer portion 12 was similar to that from the outer layer portion 13 at 50 rotations/minute. The dissolution rates of Compound I from the outer layer portions 12 and 13 at 200 rotations/minute were faster than the dissolution rates at 50 rotations/minute in a similar degree. From the above results, it was confirmed that influence of mechanical load on dissolution was similar in the dissolution behavior for the outer layer portion tablet 12 and the outer layer portion tablet 13.

Test Example 11

Figure 11:
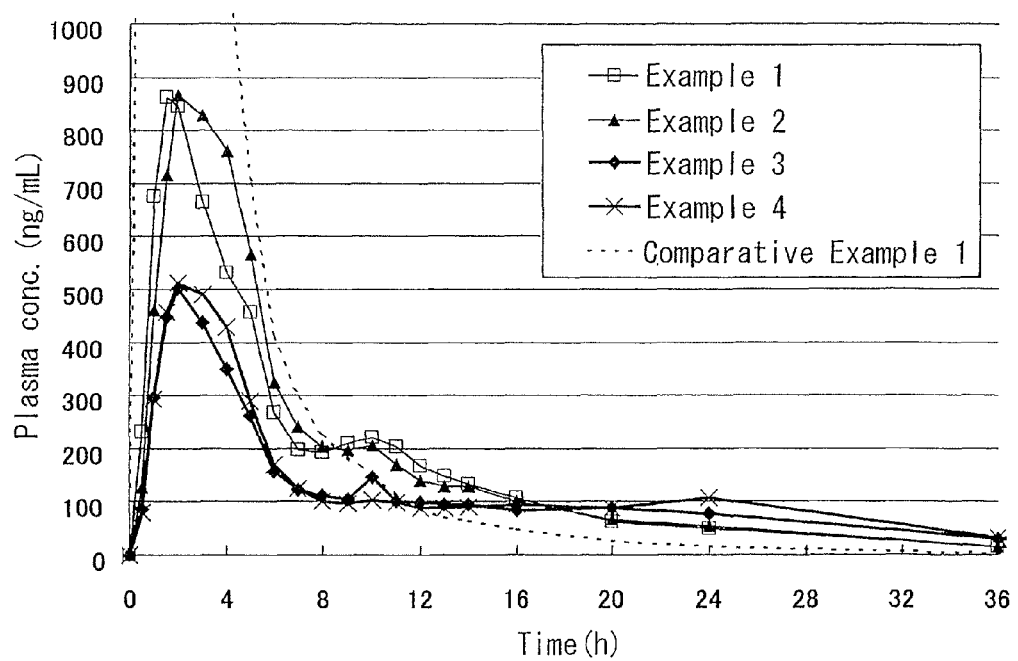
FIG. 11 shows the results of the PK study in humans in Test Example 11.

A total of 5 preparations, the coat-core tablets (containing 80 mg of Compound I) of Examples 1, 2, 3 and 4 and the tablet (containing 80 mg of Compound I) of Comparative Example 1, were administered orally to 35 healthy adults once daily under fasting in 5 separate periods by a cross-over method. The wash out period between the administration was 7 days. Blood was collected from the subjects over time after administration, and the concentrations of Compound I in the plasma were quantified. The graph showing the changes in the plasma concentration of Compound I after administration of these preparations is shown in FIG. 11, and the pharmacokinetic parameters are shown in Table 17.

TABLE 17

|  | AUC∞ (ng · hr/mL) | Cmax (ng/mL) |
| --- | --- | --- |
| Example 1 | 6678.30 | 1087.55 |
| Example 2 | 7582.64 | 1188.67 |
| Example 3 | 4874.19 | 597.18 |
| Example 4 | 5761.41 | 670.94 |
| Comparative Example 1 | 10544.62 | 3574.00 |

The invention claimed is:

1. A controlled release tablet comprising an inner core and an outer layer portion covering the inner core, wherein the inner core contains 2-(3-cyano-4-isobutyloxyphenyl)-4-methyl-5-thiazole carboxylic acid and the outer layer portion is a sustained release matrix layer and contains 2-(3-cyano-4-isobutyloxyphenyl)-4-methyl-5-thiazole carboxylic acid and a gel-forming water-soluble polymer in an amount of 16% (w/w) or more with respect to the weight of the outer layer portion.

2. The controlled release tablet according to claim 1, wherein the outer layer portion contains no water-insoluble polymer.

3. The controlled release tablet according to claim 1, wherein the gel-forming water-soluble polymer is contained in an amount in the range of 20 to 60% (w/w) with respect to the weight of the outer layer portion.

4. The controlled release tablet according to claim 1, wherein the gel-forming water-soluble polymer is contained in an amount in the range of 35 to 45% (w/w) with respect to the weight of the outer layer portion.

5. The controlled release tablet according to claim 1, wherein the gel-forming water-soluble polymer is hydroxypropylcellulose, or hydroxypropylmethylcellulose, or methylcellulose.

6. The controlled release tablet according to claim 1, wherein the gel-forming water-soluble polymer is hydroxypropylmethylcellulose.

7. The controlled release tablet according to claim 6, wherein the hydroxypropylmethylcellulose is the one having a viscosity ranging between about 80 to about 120 mPa·s or about 3,000 to about 5,600 mPa·s in terms of a 2% (w/w) aqueous solution at 20° C.

8. The controlled release tablet according to claim 6, wherein the content of the hydroxypropylmethylcellulose having a viscosity ranging between about 80 to about 120 mPa·s in terms of a 2% (w/w) aqueous solution at 20° C. is 35 to 45% (w/w) with respect to the weight of the outer layer portion.

9. The controlled release tablet according to claim 6, wherein the content of the hydroxypropylmethylcellulose having a viscosity of about 80 to about 120 mPa·s in terms of a 2% (w/w) aqueous solution at 20° C. is in a range between 17.5 and 22.5% (w/w) with respect to the weight of the outer layer portion in mixture with the content of the hydroxypropylmethylcellulose having a viscosity of about 3,000 to about 5,600 mPa·s in terms of a 2% (w/w) aqueous solution at 20° C. is in a range between 17.5 and 22.5% (w/w) with respect to the weight of the outer layer portion.

10. The controlled release tablet according to claim 1, wherein the inner core contains a disintegrant.

11. The controlled release tablet according to claim 10, wherein the disintegrant is croscarmellose sodium.

12. The controlled release tablet according to claim 11, wherein the content of croscarmellose sodium is in a range between 1 and 20% (w/w) with respect to the weight of the inner core.

13. The controlled release tablet according to claim 1, wherein an average particle diameter of 2-(3-cyano-4-isobutyloxyphenyl)-4-methyl-5-thiazole carboxylic acid contained in the inner core is in a range between 1.0 and 5.0 μm.

14. The controlled release tablet according to claim 1, wherein 2-(3-cyano-4-isobutyloxyphenyl)-4-methyl-5-thiazole carboxylic acid contained in the outer layer portion is dissolved at a constant rate, and then 2-(3-cyano-4-isobutyloxyphenyl)-4-methyl-5-thiazole carboxylic acid contained in the inner core starts to be dissolved, and a dissolution rate of 2-(3-cyano-4-isobutyloxyphenyl)-4-methyl-5-thiazole carboxylic acid from the inner core is 85% or higher at 10 minutes in the dissolution test using the paddle method of the dissolution test of the Japanese Pharmacopoeia.

15. The controlled release tablet according to claim 14, wherein the dissolution rate of 2-(3-cyano-4-isobutyloxyphenyl)-4-methyl-5-thiazole carboxylic acid in the dissolution test using modified paddle method of the dissolution test of the Japanese Pharmacopoeia with a stationary basket is 5 to 25% at 60 minutes, 30 to 50% at 150 minutes, and 80% or higher at 240 minutes, after the start of the test.

16. The controlled release tablet according to claim 14, wherein the dissolution rate of 2-(3-cyano-4-isobutyloxyphenyl)-4-methyl-5-thiazole carboxylic acid in the dissolution test using modified paddle method of the dissolution test of the Japanese Pharmacopoeia with a stationary basket is 5 to 25% at 120 minutes, 30 to 50% at 300 minutes, and 80% or higher at 480 minutes, after the start of the test.

* * * * *